(12) United States Patent
Fukutani (10) Patent No.: US 10,206,586 B2
(45) Date of Patent: Feb. 19, 2019

(54) SPECIMEN INFORMATION ACQUISITION APPARATUS AND METHOD THEREFOR

(71) Applicant: CANON KABUSHIKI KAISHA, Tokyo (JP)

(72) Inventor: Kazuhiko Fukutani, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/386,687

(22) Filed: Dec. 21, 2016

(65) Prior Publication Data

US 2017/0100039 A1 Apr. 13, 2017

Related U.S. Application Data

(63) Continuation of application No. 14/112,228, filed as application No. PCT/JP2012/059950 on Apr. 5, 2012, now Pat. No. 9,554,709.

(30) Foreign Application Priority Data

Apr. 18, 2011 (JP) .................................. 2011-092155

(51) Int. Cl.
| | |
|---|---|
| *A61B 5/00* | (2006.01) |
| *A61B 5/02* | (2006.01) |
| *G01N 21/17* | (2006.01) |
| *G01N 29/24* | (2006.01) |

(52) U.S. Cl.
CPC ........ *A61B 5/0095* (2013.01); *A61B 5/02007* (2013.01); *A61B 5/7485* (2013.01); *G01N 21/1702* (2013.01); *G01N 29/2418* (2013.01); *A61B 2576/00* (2013.01); *G01N 2291/02466* (2013.01)

(58) Field of Classification Search
CPC ............................ A61B 5/0095; A61B 5/7485
See application file for complete search history.

(56) References Cited

U.S. PATENT DOCUMENTS

2010/0094561 A1* 4/2010 Masumura ........... A61B 5/0073
702/19

OTHER PUBLICATIONS

Cox, B.T., et al., "Quantitative Photoacoustic Image Reconstruction for Molecular Imaging", Proc of SPIE, Feb. 9, 2006, vol. 6086, No. 60861M.

* cited by examiner

*Primary Examiner* — Joseph M Santos Rodriguez
(74) *Attorney, Agent, or Firm* — Canon USA Inc., IP Division (57) ABSTRACT

An apparatus includes a detector to output a signal by detecting an acoustic wave produced by irradiating a specimen with light, and a processor configured to: calculate a first optical characteristic value distribution in the specimen; determine, based on a designation by an operator for the first optical characteristic value distribution, two or more regions of a vessel in the specimen; calculate, by using an initial sound pressure distribution or optical energy absorption density distribution of the two or more regions of the vessel, an average optical constant of a background region which surrounds the two or more regions of the vessel; calculate, by using the average optical constant of the background region, a local fluence distribution in the specimen; and calculate, by dividing the first optical characteristic value distribution by the local fluence distribution, a second optical characteristic value distribution in which the first optical characteristic value distribution is corrected.

30 Claims, 5 Drawing Sheets

SPECIMEN INFORMATION ACQUISITION APPARATUS AND METHOD THEREFOR

CROSS-REFERENCE TO RELATED APPLICATIONS

This application is a Continuation of co-pending U.S. patent application Ser. No. 14/112,228, filed Oct. 16, 2013, which is a U.S. national stage application of International Patent Application No. PCT/JP2012/059950, filed Apr. 5, 2012, which claims the priority benefit of Japanese Patent Application No. 2011-092155 filed Apr. 18, 2011, all of which are hereby incorporated by reference herein in their entirety.

TECHNICAL FIELD

The present invention relates to a specimen information acquisition apparatus which generates an optical characteristic value distribution of a specimen by using photoacoustic waves, and a method used for the specimen information acquisition apparatus to acquire specimen information.

BACKGROUND ART

Research on optical imaging apparatuses which emit light from a light source such as a laser into a living body and which create images that represent information about the inside of the living body which is obtained on the basis of the incident light has been actively carried out in the medical field. One technique in this optical imaging technology is photoacoustic imaging (PAI). In PAI, a living body is irradiated with pulsed light produced from a light source, acoustic waves (typically, ultrasonic waves) are detected which are produced from the tissue of the living body that absorbs the energy of the pulsed light which propagates and diffuses in the living body, and imaging (creation of an image) is performed on the basis of the detected signals so that the created image represents live body information. That is, by utilizing a difference between the light energy absorption ratio of a specimen area such as a tumor and that of other tissue of the specimen, elastic waves which are produced when the specimen area absorbs received light energy and momentarily expands are detected by an acoustic wave probe (also referred to as a probe or a transducer) which is a detector. The detected signals are analyzed so that an image that represents an optical characteristic value distribution, such as an initial pressure distribution, an optical energy absorption density distribution, or an optical absorption coefficient distribution, is obtained.

These pieces of image information can be utilized for quantitative measurement of a specific substance in a specimen, such as hemoglobin concentration included in blood, or oxygen saturation of blood, by measuring the specimen by means of light having various wavelengths.

Recently, by using this photoacoustic imaging, preclinical research on imaging of a vessel image of a small animal, and clinical research on application of this principle to diagnosis of, for example, breast cancer, prostatic cancer, and carotid plaque have been actively carried out.

In photoacoustic imaging, an initial sound pressure ($P_0$) for photoacoustic waves produced from an absorber due to light absorption may be expressed by the following equation.

[Math. 1]

$$P_0 = \Gamma \cdot \mu_a \cdot \Phi \quad (1)$$

Here, $\Gamma$ represents a Grueneisen coefficient, which is obtained by dividing the product of a thermal expansion coefficient ($\beta$) and the square of the speed of sound (c) by a specific heat at constant pressure ($C_P$). The symbol $\mu_a$ represents the optical absorption coefficient of an absorber, and $\Phi$ represents a quantity of light (local optical fluence) with which the absorber is irradiated. The Grueneisen coefficient $\Gamma$ is known to have a substantially constant value for the same tissue. Accordingly, by measuring and analyzing changes in a sound pressure P, which is the magnitude of an acoustic wave, in multiple positions, the product of $\mu_a$ and $\Phi$, that is, an optical energy absorption density distribution can be obtained.

In photoacoustic imaging, as understandable from Equation (1) described above, to determine an absorption coefficient ($\mu_a$) distribution in a specimen, which is required for quantitative imaging, from the measurement result of a sound pressure (P), it is necessary to determine a quantity of light ($\Phi$), with which an absorber that produces photoacoustic waves is irradiated, in some way. However, light introduced into the inside of a specimen (especially, a living body) exhibits behavior such as strong diffusion, so that it is difficult to estimate a quantity of light with which an absorber is irradiated.

Therefore, when no specific measures are taken, photoacoustic imaging has a problem in that only an image that represents an optical energy absorption density ($\mu_a \times \Phi$) distribution or an initial sound pressure ($P_0$) distribution obtained by multiplying the optical energy absorption density distribution by $\Gamma$ can be generated on the basis of the measurement results of sound pressures of acoustic waves. For example, even when light absorbers are composed of the same substance and have the same absorption coefficient, such light absorbers are displayed in different contrasts in accordance with an influence of a local fluence distribution in the living body (for example, a distance from a light source).

CITATION LIST

Non Patent Literature

NPL 1 "Photoacoustic imaging in biomedicine", M. Xu, L. V. Wang, REVIEW OF SCIENTIFIC INSTRUMENT, 77, 041101, 2006

SUMMARY OF INVENTION

Technical Problem

As described above, photoacoustic imaging has a problem in that it is difficult to precisely compute a local fluence distribution ($\Phi$) with which an absorber is irradiated, and, as a result, it is difficult to compute an optical characteristic value distribution such as an absorption coefficient distribution properly.

Therefore, the present invention provides a specimen information acquisition apparatus which can obtain an optical characteristic value distribution in which an influence of a local fluence distribution ($\Phi$) with which an absorber is irradiated is reduced, and a method for acquiring specimen information.

Solution to Problem

To overcome the above-described problem, there is provided a specimen information acquisition apparatus including a light source, a detector, and a signal processing apparatus. The light source irradiates a specimen with light. The detector detects an acoustic wave that is produced by the specimen due to the light. The signal processing apparatus generates an optical characteristic value distribution of the specimen on the basis of a detected signal that is obtained from the detector. The signal processing apparatus includes a region extraction unit and an optical constant estimation unit. The region extraction unit extracts two or more regions that have a known absorption coefficient, from the optical characteristic value distribution of the specimen. The optical constant estimation unit estimates an optical constant of a background of the specimen by using optical characteristic values of the two or more regions extracted by the region extraction unit and a local fluence distribution obtained from an optical constant that is set in advance for the specimen background.

Advantageous Effects of Invention

The present invention can provide a specimen information acquisition apparatus which can obtain an optical characteristic value distribution in which an influence of a local fluence distribution ($\Phi$) with which an absorber is irradiated is reduced, and a method for acquiring specimen information.

DESCRIPTION OF EMBODIMENTS

The present invention will be described in more detail below referring to the drawings. In principle, the same components are designated with the same reference numeral, and will not be described.

Figure 1:
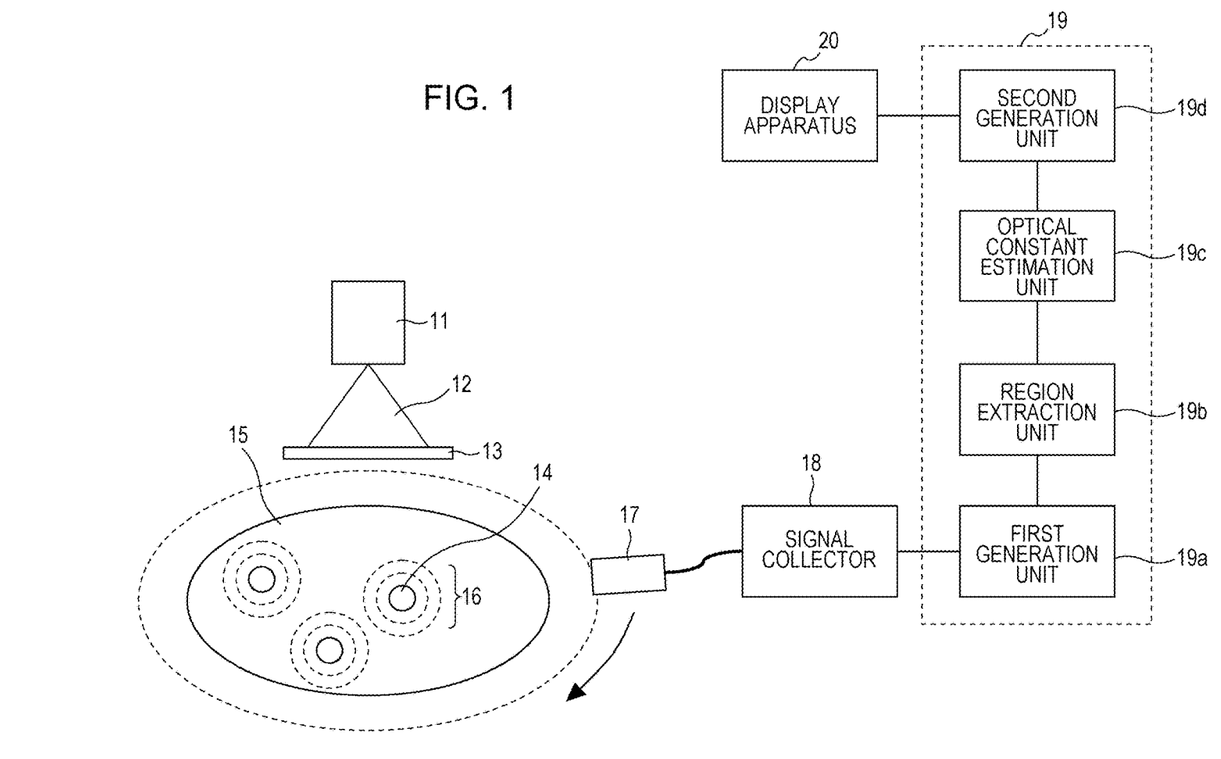
FIG. 1 is a schematic diagram illustrating a configuration of a specimen information acquisition apparatus according to an embodiment of the present invention.

Referring to FIG. 1, a configuration of a specimen information acquisition apparatus according to an embodiment of the present invention will be described. The specimen information acquisition apparatus according to the embodiment is an apparatus which creates an image that represents optical characteristic value information about the inside of a specimen.

Herein, the optical characteristic value information typically indicates an initial sound pressure distribution ($P_0$) or an optical energy absorption density distribution ($\mu_a \cdot \Phi$), or an optical absorption coefficient distribution ($\mu_a$) which is derived from these.

Basic Configuration

The specimen information acquisition apparatus according to the embodiment has a basic hardware configuration including a light source 11, a detector 17, and a signal processing apparatus 19. Pulsed light 12 emitted from the light source 11 is guided while being processed by an optical system including, for example, a lens, a mirror, an optical fiber, and a diffuser plate so as to be shaped in a desired form, and enters a specimen 15 such as a living body.

When part of optical energy that propagates through the inside of the specimen 15 is absorbed into light absorbers 14 such as vessels, acoustic waves 16 which are elastic waves are produced due to thermal expansion of the light absorbers 14. These may be called "photoacoustic waves".

The acoustic waves 16 are detected by the detector 17, and are amplified and converted into digital signals by a signal collector 18. Then, an optical characteristic value distribution for the specimen 15 is generated by the signal processing apparatus 19, and is output as image data. This image data is displayed as an image on a display apparatus 20.

Method for Acquiring Specimen Information

An exemplary method for acquiring specimen information which is performed by the signal processing apparatus 19 and which is a characteristic of the present invention will be described referring to the drawings. The reference numerals in the description each correspond to the number of a corresponding one of the processes in FIG. 2.

Figure 2:
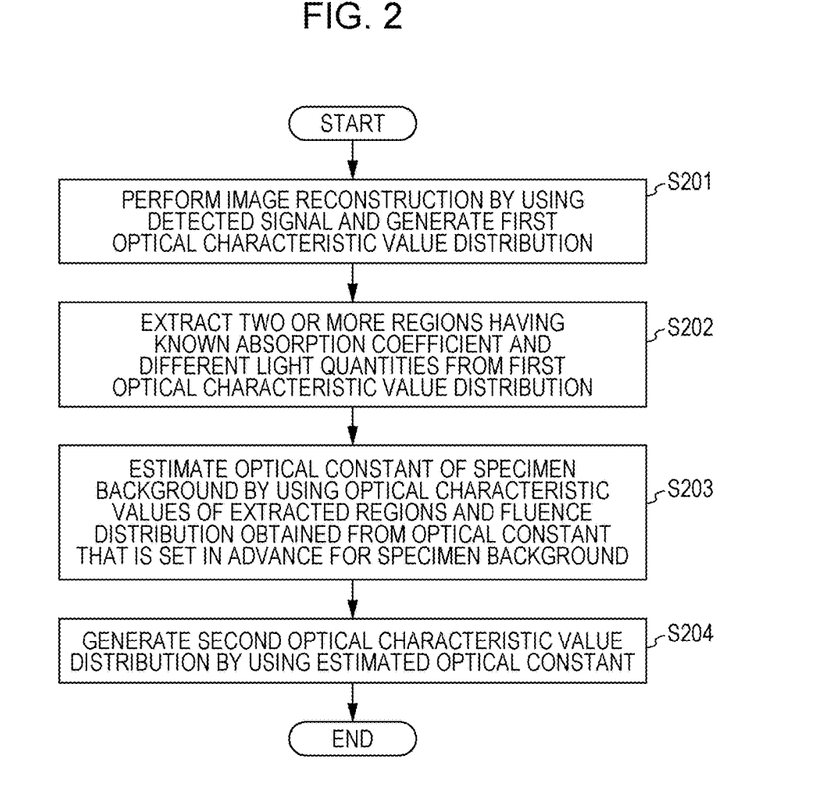
FIG. 2 is a flowchart of an exemplary process on detected signals according to an embodiment of the present invention.

In step S201, an optical characteristic value distribution is generated. In this step, image reconstruction is performed using received signals so that the optical characteristic value distribution (first optical characteristic value distribution) for the specimen is generated. Here, an optical characteristic value distribution for a specimen means an initial sound pressure distribution or an optical energy absorption density distribution which is obtained by multiplying an absorption coefficient distribution by a local fluence distribution, which are expressed by, for example, Equation (1). This first optical characteristic value distribution is dependent on the local fluence distribution.

For example, a first generation unit 19a generates the first optical characteristic value distribution by using received digital signals which are detected signals and which are obtained from the signal collector 18.

This process can be performed by using various image reconstruction processes used in typical photoacoustic imaging. For example, a time-domain back-projection method and a Fourier transform method, which are typically used in tomography technology, may be used as an image reconstruction algorithm. When it is possible to take a large amount of time for the reconstruction, an image reconstruction technique such as a model-based method that performs a large number of matrix operations may be used. Typical image reconstruction techniques for PAI include a Fourier transform method, a back-projection method, a time reversal method, a deconvolution method, and a model-based method. In the present invention, any image reconstruction technique may be used.

When, for example, a focus-type detector that performs detection for limited observation points is used and a received signal from such a detector is originally proportional to an image in the depth direction, the image reconstruction need not be performed and the received signal may be directly converted into image data.

In step S202, two or more regions from the optical characteristic value distribution is extracted. In this step, two or more regions that have known absorption coefficients are extracted from the first optical characteristic value distribution which is generated in step S201. As long as the absorption coefficients of the two or more regions are known, the absorption coefficients of the regions may be the same or may be different. In addition, as long as the regions to be extracted have any quantitative data, the regions are not necessarily image data.

Figure 6A:
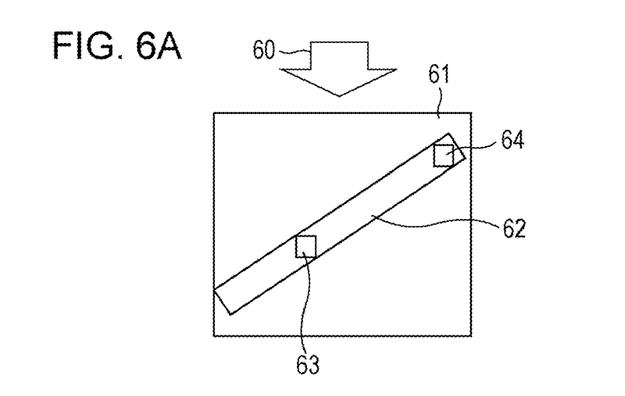
FIGS. 6A to 6C are diagrams for explaining examples in which two or more regions are extracted from an optical characteristic value distribution.

FIG. 6A illustrates an exemplary method for extracting regions. Since light 60 with which a specimen 61 is irradiated is attenuated in accordance with the incident depth, light quantities during the irradiation are different in regions 63 and 64 in a vessel 62. Since the regions 63 and 64 are portions of the same vessel, the absorption coefficients of these regions are the same. In this step, two or more regions may be extracted from the same light absorber as described above.

Figure 6B:
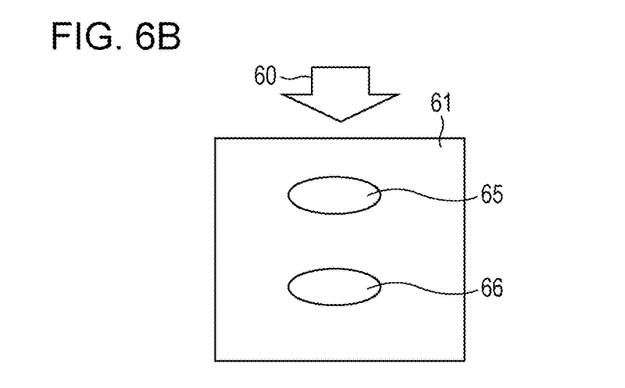

FIG. 6B illustrates an example in which two or more regions are extracted from different light absorbers. Thus, in this step, as long as the absorption coefficients of regions 65 and 66 are known, these regions may be extracted. For example, a contrast agent that has an absorption coefficient that is known in advance may be introduced and utilized.

Figure 6C:
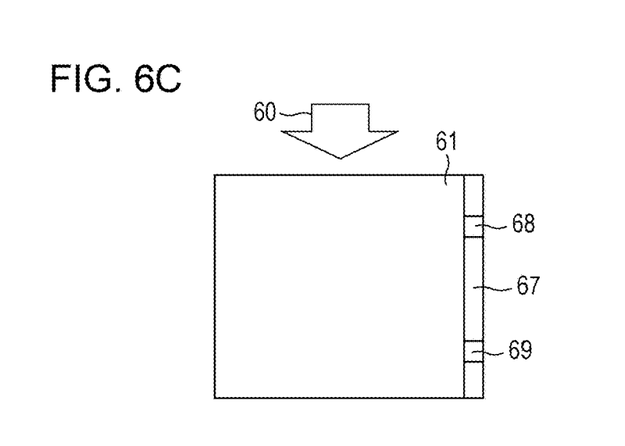

FIG. 6C illustrates an example in which two or more regions are extracted from a light absorber provided on the outside of the specimen 61. Thus, in this step, a light absorber 67 may be provided on the outside of the specimen 61, and regions 68 and 69 which are portions of the light absorber 67 may be extracted.

The apparatus may automatically extract regions, or an operator using the apparatus may specify regions, so that the regions are extracted.

For example, a region extraction unit 19b extracts, for example, image data regions that have the same absorption coefficient from an image that represents the first optical characteristic value distribution obtained by the first generation unit 19a. That is, positions in which the absorption coefficients are the same in at least one light absorber are specified from image data of the at least one light absorber.

Figure 3A:
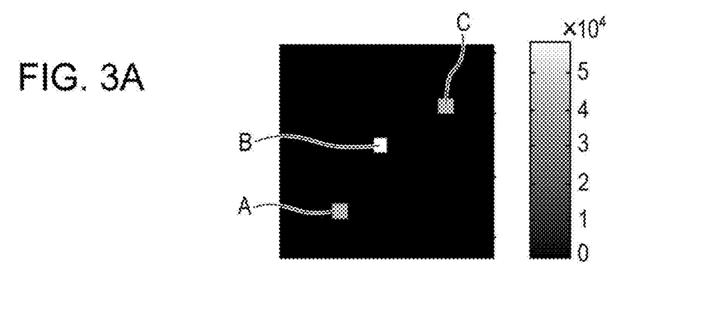
FIG. 3A is a diagram illustrating an exemplary image.

FIG. 3A illustrates an example of the first optical characteristic value distribution obtained through the process performed in step S201. In FIG. 3A, the regions denoted by reference characters A, B, and C represent light absorbers which have been subjected to imaging. The contrast (color intensity) of each region represents, for example, the magnitude of the initial sound pressure or the optical energy absorption density. Although the absorption coefficients of the light absorbers corresponding to the reference characters A, B, and C in FIG. 3A are the same, the contrasts are different.

In step S203, optical constants of a specimen background is estimated. In this step, the optical constants of the specimen background are estimated by using optical characteristic values, such as initial sound pressures or optical energy absorption densities, of the two or more regions extracted in step S202, and optical constants which are set in advance for the specimen background.

The optical constants of the specimen background that are to be estimated in this step include, for example, an absorption coefficient ($\mu_a^b$), a scattering coefficient ($\mu_s^b$), and an anisotropic parameter ($g^b$) of the specimen background. A scattering coefficient ($\mu_s^b$) and an anisotropic parameter ($g^b$) are included in a reduced scattering coefficient ($\mu_s'^b$), and an absorption coefficient ($\mu_a^b$) and a reduced scattering coefficient ($\mu_s'^b$) may be obtained as the optical constants of the specimen background. Furthermore, an absorption coefficient ($\mu_a^b$) and a reduced scattering coefficient ($\mu_s'^b$) are included in an effective attenuation coefficient ($\mu^b_{eff}$), and an effective attenuation coefficient ($\mu^b_{eff}$) may be obtained as the optical constant of the specimen background.

For example, an optical constant estimation unit 19c estimates the optical constants of the specimen background from pieces of extracted image data that have the same absorption coefficient. In the following description, an absorption coefficient and a reduced scattering coefficient are estimated as an example of the optical constants of the specimen background.

In the case where the specimen is a living body, when the emitted light is near-infrared light of 500 to 900 nm, the main light absorber in the living body is oxygenated/deoxygenated hemoglobin. In other words, an image of vessels having a large amount of hemoglobin is mainly created. Here, it is assumed that the absorption coefficients of blood in vessels located in any positions be the same.

Under this assumption, the values of an absorption coefficient ($\mu_a$) and a Grueneisen coefficient ($\Gamma$) in Equation (1) are constant in a vessel image. That is, $\Gamma$ and $\mu_a$ are constants, so that $P_0(r)$ is a function that is dependent only on a local fluence distribution $\Phi(r)$. The local fluence distribution $\Phi(r)$ may be obtained through calculation when the optical constants, the shape, the light irradiation distribution (light source distribution) of the specimen are determined.

Specific description will be made using equations. It is assumed that the initial sound pressure distribution $P_0(r)$ is obtained as the first optical characteristic value distribution. In addition, it is assumed that the quantity of light at a position r of a light absorber is determined by the absorption coefficient ($\mu_a^b$) and the reduced scattering coefficient ($\mu_a'^b$) of the specimen background. Equation (1) will be the following equation.

[Math. 2]

$$P_0(r) = \Gamma(r) \cdot \mu_a(r) \cdot \Phi(r, \mu_a^b, \mu_s'^b) \qquad (2)$$

Here, r represents a position of the light absorber. It is assumed that all of the light absorbers are vessels, and that the absorption coefficients ($\mu_a$) of the vessels are constant regardless of the oxygen saturation. In this case, $\Gamma$ and $\mu_a$ are constants. Consequently, $P_0(r)$ is a function that is dependent only on the local fluence distribution ($\Phi$).

[Math. 3]

$$P_0(r) \approx A \cdot \Phi(r, \mu_a^b, \mu_s'^b) \qquad (3)$$

Here, A is a proportional constant, and is obtained by multiplying the $\Gamma$ by $\mu_a$, which are constants. When the specimen background is a uniform medium and diffusion approximation for light is established, the quantity of light $\Phi(r)$ at a position r of the light absorber may be obtained using, for example, the following diffusion equation.

[Math. 4]

$$\mu_a^b \cdot \Phi(r) - D\nabla^2 \Phi(r) = S(r) \qquad (4)$$

Here, D is a diffusion constant, and is expressed by the equation $D = 1/3 \ (\mu_a^b + \mu_s'^b)$, and S(r) represents a light irradiation distribution. In other words, when optical constants of the specimen background, such as a diffusion constant D and an absorption coefficient $\beta_a^b$, boundary conditions such as the shape of the specimen, and a light irradiation distribution S(r) are determined, the local fluence distribution $\Phi(r)$ of the specimen background may be obtained through forward model calculation (simulation). Here, it is assumed that the absorption coefficient ($\mu_a^b$) and the reduced scattering coefficient ($\mu_s^b$) of the specimen background be variables, and the local fluence distribution obtained through calculation is defined as $\Phi_{sim}(r, \mu_a^b, \mu_s^b)$.

Then, an objective function E is defined as follows.

[Math. 5]

$$E = \sum_r \sqrt{[P_0(r) - A \cdot \Phi_{sim}(r, \mu_a^b, \mu_s'^b)]^2} \quad (5)$$

By minimizing the objective function E, an absorption coefficient ($\mu_a^b$) and a reduced scattering coefficient ($\mu_s'^b$), which are the optical constants of the specimen background, may be estimated. Specifically, a typical optimization technique is used, and while the absorption coefficient and the reduced scattering coefficient are repeatedly updated and $\Phi_{sim}$ is obtained through simulation, E may be minimized. For example, the absorption coefficient ($\mu_a^b$) and the reduced scattering coefficient ($\mu_s'^b$), which are the optical constants of the specimen background, are set as appropriate, and a local fluence distribution $\Phi_{sim}(r, \mu_a^b, \mu_s'^b)$ of the specimen is calculated through simulation.

The average absorption coefficient ($\mu_a^b$) and the average reduced scattering coefficient ($\mu_s'^b$) of the specimen background are repeatedly changed so as to cause the minimization of a sum of the differences between the result obtained by multiplying the value $\Phi_{sim}(r, \mu_a^b, \mu_s'^b)$ by the predetermined proportional constant A and each of the pieces of image data that have the same absorption coefficient and that are obtained in step S202.

Figure 3B:
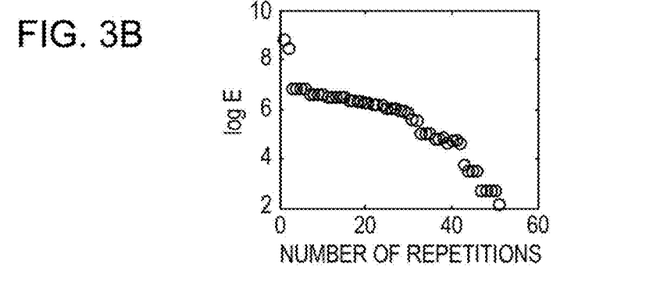
FIGS. 3B to 3D are graphs showing calculation results.

For example, FIG. 3B illustrates the result obtained through the above-described minimization. The vertical axis represents a log value of the objective function E, and the horizontal axis represents the number of repetitions of the calculation.

Figure 3C:
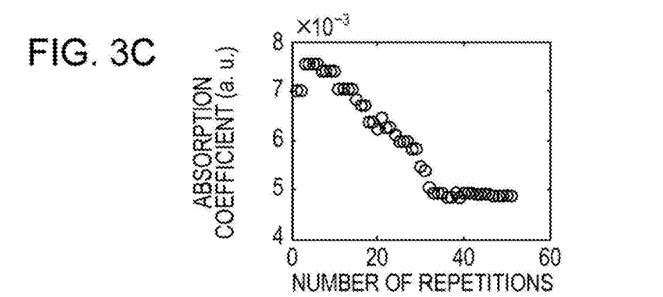
Figure 3D:
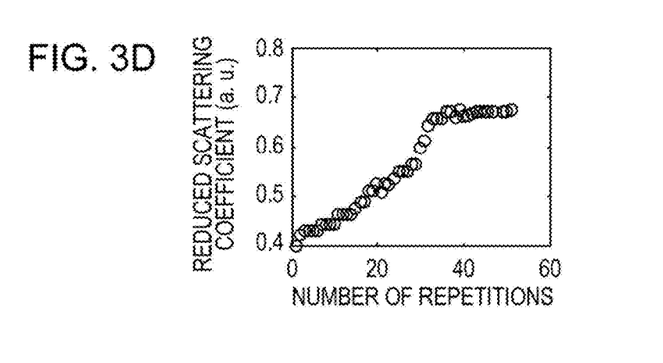

FIG. 3C illustrates the relationship between an absorption coefficient of the specimen background and the number of repetitions of the calculation. FIG. 3D illustrates the relationship between a reduced scattering coefficient of the specimen background and the number of repetitions of the calculation. From these graphs, it is found that the value of the objective function E becomes small through the optimization computation (FIG. 3B), and that the absorption coefficient and the reduced scattering coefficient converge on certain values as the value of the objective function E becomes small (FIGS. 3C and 3D). The final convergence values are defined as average optical constants of the specimen background.

As described above, by using such a repeated computation method, the optical constants of the specimen background may be estimated from an optical characteristic value distribution, such as an initial sound pressure distribution or an optical energy absorption density distribution.

When the light absorber is a vessel, the absorption coefficient of the vessel varies in accordance with oxygen saturation. Accordingly, a certain wavelength that causes the absorption coefficient not to vary in accordance with an oxygen saturation value, for example, a wavelength of 797 nm, is desirably selected.

In the above-described embodiment, certain examples, such as a method for estimating a local fluence distribution, an objective function, and an optimization technique for the objective function are employed. However, any methods and techniques may be used as the method for estimating a local fluence distribution, a method for selecting an objective function, and the optimization technique for the objective function as long as the optical constants of the specimen background are eventually determined by using these.

By performing the step described above, optical constants of the specimen background may be estimated from pieces of image data that have the same absorption coefficient.

In step S204, an optical characteristic value distribution by using the estimated optical constant is generated. In this step, a local fluence distribution is computed using the optical constants of the specimen background that are estimated in step S203, and the optical characteristic value distribution (second optical characteristic value distribution) of the specimen is generated by using the values of this local fluence distribution. The second optical characteristic value distribution is, for example, an optical absorption coefficient distribution in which an influence of the local fluence distribution is reduced.

Figure 4:
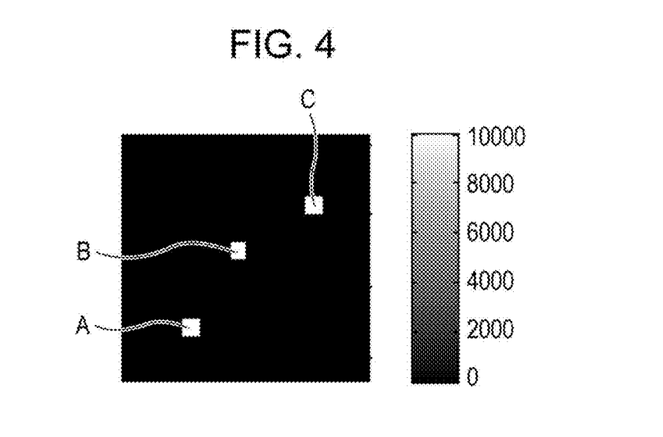
FIG. 4 is a diagram illustrating an exemplary image in which an influence of a local fluence distribution is reduced.

For example, a second generation unit 19d computes a local fluence distribution in the specimen by using the optical constants of the specimen background obtained in step S203 and, for example, the diffusion equation expressed by Equation (4). Then, by using the obtained local fluence distribution, the first optical characteristic value distribution obtained in step S201 is corrected. FIG. 4 illustrates an optical characteristic value distribution obtained by dividing the first optical characteristic value distribution in FIG. 3A by the local fluence distribution computed using the absorption coefficient and the reduced scattering coefficient of the specimen background that are obtained from the results in FIGS. 3C and 3D. In FIG. 3A, the light absorbers A, B, and C that have the same absorption coefficient are represented by images having different contrasts due to the influence of the local fluence distribution. In contrast, in FIG. 4, the light absorbers are represented by images having the same contrast. That is, the second optical characteristic value distribution in which the influence of the local fluence distribution is reduced is obtained.

As described above, an example in which a local fluence distribution is obtained using a diffusion equation is described. However, any method, such as a method in which a radiative transport equation is precisely solved, or the Monte Carlo method, may be employed as long as a local fluence distribution is obtained.

As described above, the second optical characteristic value distribution is obtained by dividing the first optical characteristic value distribution by the local fluence distribution. However, other computation methods may be used to obtain the second optical characteristic value distribution.

By performing the above steps, even when the optical constants for the specimen are not known, a specimen information acquisition apparatus can be provided which can obtain an image in which an influence of the local fluence distribution in a specimen is reduced.

The first generation unit 19a, the region extraction unit 19b, the optical constant estimation unit 19c, and the second generation unit 19d are functional blocks, which are typically performed by software. The execution of the software may be performed in the same hardware, or may be performed in different pieces of hardware.

Now, an exemplary specific configuration according to the embodiment will be described.

Light Source 11

When the specimen is a living body, the light source 11 emits light having a certain wavelength which is absorbed by a specific one of the components of the living body. The light source may be provided integrally with the specimen information acquisition apparatus according to the embodiment, or may be provided separately from the specimen information acquisition apparatus. The light source is desirably a pulsed light source that can generate pulsed light on the order of several to hundreds nano-seconds. Specifically, to generate photoacoustic waves efficiently, the pulse width of about 10 nano-seconds is used. A laser is desirably used as the light source because it produces a large amount of output. Instead of a laser, for example, a light-emitting diode may be used. Various lasers, such as a solid laser, a gas laser, a dye laser, and a semiconductor laser, may be used. A light source controller (not illustrated) controls, for example, the timing of the irradiation and optical intensity. This light source controller is typically provided integrally with the light source. Usable wavelengths of the light source are desirably wavelengths that cause light to propagate into the inside of the specimen. Specifically, when the specimen is a living body, the wavelength is equal to or more than 500 nm and equal to or less than 1200 nm.

Light Absorber 14 and Specimen 15

The light absorber 14 and the specimen 15, which are not included in the specimen information acquisition apparatus according to the embodiment of the present invention, will be described below. The specimen information acquisition apparatus according to the embodiment of the present invention which uses photoacoustic waves aims to be mainly used for angiography, diagnosis for malignant tumors, vascular diseases, or the like for a human being or an animal, observation after chemotherapy, or the like. Accordingly, it is presumed that the specimen 15 is a living body, particularly, a part to be checked for diagnosis, such as a breast, a finger, or a limb of a human being or an animal. When a small animal such as a mouse is checked, the whole small animal may be checked in addition to a specific part. Components that have a relatively high absorption coefficient in the specimen are used as the light absorber 14 in the specimen. Such components, depending on a usable light wavelength, include, for example, oxygenated or deoxygenated hemoglobin, a vessel which contains a large amount of hemoglobin, and a malignant tumor which contains many neovascular vessels, when it is assumed that a human body is to be checked.

Detector 17

The detector 17, which detects photoacoustic waves that are produced, for example, from the specimen surface and in the specimen by means of pulsed light, detects acoustic waves and converts the acoustic waves into electric signals which are analog signals. This detector may be a probe or a transducer. Any detector, such as a transducer using piezoelectric phenomena, a transducer using optical resonance, or a transducer using changes in capacitance, may be used as long as the detector detects an acoustic wave signal. It is desirable that the detector 17 according to the embodiment be typically a detector in which sensing elements are arranged in one or two dimensions. Such multidimensional array elements are used so that acoustic waves can be simultaneously detected in multiple positions, thereby reducing the measurement time. As a result, an influence of the vibration of the specimen or the like can be reduced. If scanning is performed using a single detector having only one detector in such a manner that acoustic waves can be detected in multiple positions, a one or two dimensional array detector need not be used. As in FIG. 1, scanning is performed using the detector 17 in a region surrounding the specimen 15, or multiple detectors are prepared like an array-type detector, so that the acoustic waves 16 are desirably detected at various angles.

Signal Collector 18

The specimen information acquisition apparatus according to the embodiment desirably has the signal collector 18 which amplifies an electric signal obtained from the detector 17 and converts the electric signal, which is an analog signal, into a digital signal. The signal collector 18 typically includes an amplifier, an A/D converter, and a field programmable gate array (FPGA) chip. When the signal collector 18 obtains multiple detected signals from the detector 17, it is desirable that the signal collector 18 can simultaneously process multiple signals. Accordingly, the time period before the formation of an image can be reduced. A term "detected signal" herein encompasses an analog signal obtained from the detector 17 and a digital signal which is a result of the A/D conversion using the analog signal.

Signal Processing Apparatus 19

The signal processing apparatus 19 performs an image reconstruction process and a computation process using the received digital signals obtained from the signal collector 18, and obtains an image in which an influence of the local fluence distribution in the specimen is reduced. In particular, the signal processing apparatus 19 according to the embodiment of the present invention performs the above-described computation process.

In general, a computer such as a workstation is typically used as the signal processing apparatus 19. The process is performed by software which is produced through programming in advance. The first generation unit 19a, the region extraction unit 19b, the optical constant estimation unit 19c, and the second generation unit 19d are typically provided as a computer such as a workstation and the software attached to the computer.

Display Apparatus 20

The display apparatus 20 displays image data that is output from the signal processing apparatus 19, and a liquid crystal display or the like is typically used as the display apparatus 20. The display apparatus 20 may be provided separately from the specimen information acquisition apparatus according to the embodiment of the present invention.

First Embodiment

An example for the specimen information acquisition apparatus using photoacoustic imaging to which the present invention is applied will be described. The description will be made using the schematic diagram illustrating the apparatus in FIG. 1.

In a first embodiment, a Q-switch YAG laser which produces pulsed light of 1064-nm wavelength and about 10 nano-seconds is used as the light source 11. The energy of the light pulse emitted from the pulsed laser light 12 is 0.6 J. An optical system is set in such a manner that the top surface of the specimen is irradiated with the pulsed light after the pulsed light is expanded so as to have a radius of about 20 mm by using a different optical system including a mirror and a beam expander.

A phantom which mimics a living body in terms of the optical constants is used as the specimen 15. The base of the phantom is made from polyurethane rubber, and the optical constants are adjusted by using titanium oxide and ink. The base phantom has an absorption coefficient of 0.0047 mm$^{-1}$ and a reduced scattering coefficient of 0.7 mm$^{-1}$.

Three columnar objects of 2-mm diameter are embedded in the base phantom as the light absorber 14. The absorption coefficients of the columnar objects are the same; the absorption coefficient is 0.08 mm$^{-1}$ and the Grueneisen coefficient is 0.9.

This phantom is placed in a water tank, the detector 17 is set so as to be operated around the phantom as illustrated in FIG. 1, and the top surface of the phantom is irradiated with the pulsed light 12. In the first embodiment, it is difficult to produce an arch-shaped array-type probe, so that a single-element-type probe is used as the detector 17.

Then, while light is emitted, scanning is performed with the detector 17, and the detector 17 receives photoacoustic waves produced in a range of 360° around the phantom.

The received analog signal is converted into digital data for the photoacoustic signal by using an amplifier, an A/D converter, and an FPGA which are included in the signal collector 18. Then, the obtained digital data is transferred to a workstation (WS) which is the signal processing apparatus 19, and is stored in the WS.

Then, the first generation unit 19a which is a software program in the WS performs image reconstruction, and computes an initial sound pressure distribution which is a photoacoustic image.

Then, the region extraction unit 19b which is a software program in the WS extracts regions that have a contrast higher than that of the surroundings from the obtained initial sound pressure distribution image, so that columnar light absorber images are extracted.

Then, the optical constant estimation unit 19c which is a software program in the WS minimizes the objective function which is the same as Equation (5). Here, the absorption coefficient and the Grueneisen coefficient of the absorber which are known in advance are used as the proportional constant A. In the minimization, the initial values of the absorption coefficient and the reduced scattering coefficient of the specimen background are set to 0.007 mm$^{-1}$ and 0.4 mm$^{-1}$, respectively. The obtained results at that time are shown in FIGS. 3B, 3C, and 3D.

In FIG. 3B, the values of the absorption coefficient and the reduced scattering coefficient of the phantom background converge after about 33 repetitions, and the final values of the absorption coefficient and the reduced scattering coefficient are 0.0049 mm$^{-1}$ and 0.68 mm$^{-1}$, respectively. These values are approximately equal to the values of the base phantom. Therefore, this method enables detection of an absorption coefficient and a reduced scattering coefficient which are average optical constants of the background of the phantom which is a specimen.

Furthermore, the second generation unit 19d which is a software program in the WS uses these values to compute the local fluence distribution in the phantom, and normalizes the initial sound pressure distribution image by using the local fluence distribution. Thus, an image in which an influence of the local fluence distribution is reduced can be obtained.

Second Embodiment

An example for a specimen information acquisition apparatus using photoacoustic imaging to which the present invention is applied will be described. In the first embodiment, an absorption coefficient ($\mu_a^b$) and a reduced scattering coefficient ($\mu_s^b$) which are optical constants of the specimen background are obtained. In a second embodiment, an effective attenuation coefficient ($\mu_{eff}^b$) which is an optical constant of the specimen background is obtained. The second embodiment is preferable when the absorption coefficient and the Grueneisen coefficient of a light absorber in a phantom are not known.

In the second embodiment, a phantom and a measurement system which are similar to those used in the first embodiment are used.

First, similarly to the first embodiment, the first generation unit 19a performs image reconstruction from received signals of photoacoustic waves so as to compute an initial sound pressure distribution, which is a photoacoustic wave image. Then, the region extraction unit 19b which is a software program in the WS extracts regions that have a higher contrast from the obtained initial sound pressure distribution image, so that columnar light absorber images are specified.

Then, an objective function is defined as follows, and a proportional constant A and an effective attenuation coefficient $\mu_{eff}^b$ of the specimen background are used as variables and are obtained so that E is minimized.

$$E = \sum_r \sqrt{[P_0(r) - A \cdot \Phi_{sim}(r, \mu_{eff}^b)]^2} \qquad \text{[Math. 6]}$$

As a result, through the repeated calculation, an effective attenuation coefficient $\mu_{eff}^b$ of the specimen background is obtained.

Furthermore, the second generation unit 19d uses this effective attenuation coefficient to compute the local fluence distribution in the phantom, and normalizes the initial sound pressure distribution image by using the local fluence distribution. Thus, an image in which an influence of the local fluence distribution is reduced can be obtained.

Third Embodiment

Figure 5:
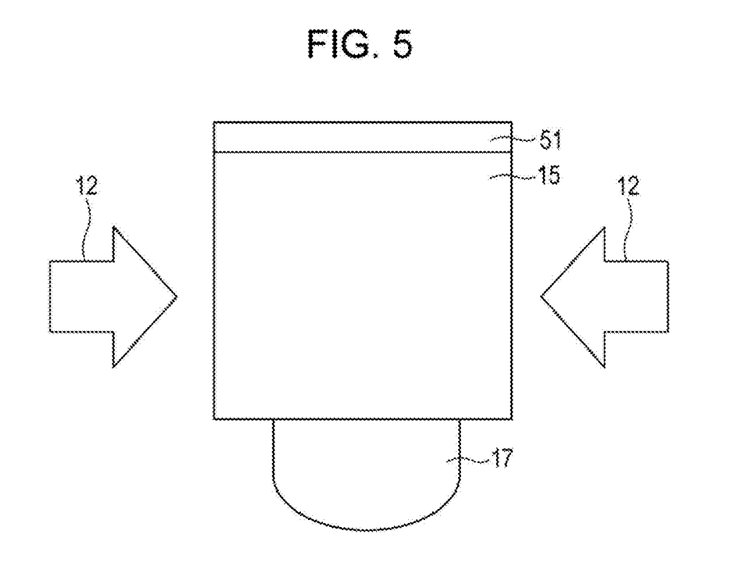
FIG. 5 is a schematic diagram illustrating an apparatus configuration which is described in a second embodiment.

An example for a specimen information acquisition apparatus using photoacoustic imaging to which the present invention is applied will be described with reference to FIG. 5. In the first and second embodiments, the optical constants of the specimen background are obtained by using light absorbers in the specimen. In a third embodiment, the optical constants of the specimen background are obtained by using a light absorber disposed on the outside of the specimen.

In the third embodiment, a Ti:sa laser which produces pulsed light of 800-nm wavelength and about 15 nanoseconds is used as the light source 11. The energy of the light pulse emitted from the pulsed laser light 12 is 0.1 J. The pulsed light is expanded so as to have a radius of about 20 mm by using an optical system including a mirror and a beam expander. A different optical system is set in such a manner that a side surface of the specimen 15 is irradiated with the pulsed light 12 as illustrated in FIG. 5.

The same phantom as that used in the first embodiment is used as the specimen 15. The base of the phantom is made from polyurethane rubber, and the optical constants are adjusted by using titanium oxide and ink.

A sheet 51 of 2-mm thickness is disposed on the top surface of the base phantom and serves as a light absorber used for estimating the optical constants. This absorber has an absorption coefficient of 0.08 mm$^{-1}$ and a Grueneisen coefficient of 0.9. The detector 17 is in contact with the bottom of this phantom.

A two dimensional (2D) array detector having multiple sensing elements arranged in two dimension is used as the detector 17. Then, produced photoacoustic waves are received by the sensing elements in the 2D array detector 17. The detected signals are converted into digital data for the photoacoustic signals by using the signal collector 18 which includes an amplifier, an A/D converter, and a FPGA. Then, the obtained digital data is transferred to the workstation (WS) which is the signal processing apparatus 19, and is stored in the WS.

Similarly to the first embodiment, the photoacoustic image obtained through the program in the WS is analyzed, and an absorption coefficient and a reduced scattering coefficient which are average optical characteristic values of the base phantom are computed. As a result, similarly to the first embodiment, values are obtained which are approximately equal to the optical constants of the phantom. Then, the second generation unit 19d uses these values to compute the local optical fluence distribution in the phantom, and normalizes the initial sound pressure distribution image by using the local fluence distribution. Thus, an image in which an influence of the local fluence distribution is reduced can be obtained.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

REFERENCE SIGNS LIST 19 signal processing apparatus
19a first generation unit
19b region extraction unit
19c optical constant estimation unit
19d second generation unit

The invention claimed is:

1. An apparatus comprising:
a light source configured to irradiate a specimen with light;
a detector configured to output a signal by detecting an acoustic wave that is produced by irradiating the specimen with the light; and
a memory in communication with a processor, the memory storing instructions that, when executed by the processor, causes the processor to:
calculate, by using the signal, a first optical characteristic value distribution in the specimen, the first optical characteristic value distribution being an initial sound pressure distribution or an optical energy absorption density distribution which represents the product of an absorption coefficient distribution and a local fluence distribution;
determine, based on a designation by an operator within the first optical characteristic value distribution, two or more regions of a vessel in the specimen;
determine from the first optical characteristic value distribution, the initial sound pressure distribution or the optical energy absorption density distribution of the determined two or more regions of the vessel;
calculate, by using the initial sound pressure distribution or the optical energy absorption density distribution of the determined two or more regions of the vessel, an average optical constant of a background region which surrounds the two or more regions of the vessel;
calculate, by using the calculated average optical constant of the background region, the local fluence distribution in the specimen; and
calculate, by dividing the first optical characteristic value distribution by the local fluence distribution, a second optical characteristic value distribution in which the first optical characteristic value distribution is corrected.

2. The apparatus according to claim 1, wherein the processor is configured to calculate, as the average optical constant, any of an average absorption coefficient, an average scattering coefficient, an average anisotropic parameter, an average reduced scattering coefficient, and an effective attenuation coefficient.

3. The apparatus according to claim 1,
wherein the processor is configured to determine, based on the designation by the operator within the first optical characteristic value distribution, the two or more regions of the vessel having a known absorption coefficient, and
wherein, when the average optical constant is a variable, the processor is configure to calculate the average optical constant of the specimen by minimizing a difference between the first optical characteristic values and a product of a light quantity obtained based on the average optical constant and a known absorption coefficient for the determined two or more regions.

4. The apparatus according to claim 1, wherein
the processor is configured to calculate a local fluence distribution in the specimen by using the average optical constant, and to calculate the second optical characteristic value distribution on the basis of the first optical characteristic value distribution and the local fluence distribution.

5. The apparatus according to claim 1, wherein the processor is configured to determine the two or more regions of the vessel having a known absorption coefficient in the specimen.

6. The apparatus according to claim 1, wherein the processor is configured to calculate, as the average optical constant, an average absorption coefficient and an average reduced scattering coefficient.

7. The apparatus according to claim 1,
wherein the processor is configured to determine, based on the designation by the operator within the first optical characteristic value distribution, the two or more regions of the vessel having a known absorption coefficient, and
wherein the processor is configured to calculate the average optical constant that satisfies a relational equation of optical characteristic values of the determined two or more regions in the first optical characteristic value distribution, local fluence values, obtained based on the average optical constant of the determined the two or more regions, and the known absorption coefficient of the determined two or more regions.

8. The apparatus according to claim 1,
wherein the processor is configured to determine, based on the designation by the operator within the first optical characteristic value distribution, the two or more regions of the vessel having a known absorption coefficient, and
wherein, when the average optical constant is a variable, the processor is configured to calculate the average optical constant, using an optimization method so that a relation between optical characteristic values in the first optical characteristic value distribution and a product of local fluence value obtained based on the average optical constant and the known absorption coefficient is satisfied in the determined two or more regions.

9. The apparatus according to claim 1, wherein the processor is configured to determine, based on the designation by the operator within the first optical characteristic value distribution, the two or more regions which are portions of a same vessel.

10. The apparatus according to claim 1, wherein the processor is configured to determine, based on the designation by the operator within the first optical characteristic value distribution, the two or more regions of the vessel having a same absorption coefficient.

11. The apparatus according to claim 1, wherein the light source is configured to irradiate the specimen with light having a wavelength of 500-900 nm.

12. The apparatus according to claim 1,
wherein the processor is configured to calculate, as the average optical constant, an average absorption coefficient and an average reduced scattering coefficient,
wherein the processor is configured to calculate, by using the average absorption coefficient and the average reduced scattering coefficient, information on a local fluence value distribution in the specimen, and
wherein the processor is configured to calculate, by using the first optical characteristic value distribution and the local fluence value distribution, an absorption coefficient distribution in the specimen.

13. The apparatus according to claim 1,
wherein the processor is configured to calculate, as the average optical constant, an effective attenuation coefficient,
wherein the processor is configured to calculate, by using the effective attenuation coefficient, a local fluence value distribution in the specimen, and
wherein the processor is configured to calculate, by using the first optical characteristic value distribution and the local fluence value distribution, an absorption coefficient distribution in the specimen.

14. A method used for an apparatus which includes a memory in communication with a processor, the memory storing instructions that, when executed by the processor, causes the processor to perform the method comprising the steps of:
calculating a first optical characteristic value distribution in a specimen on the basis of a signal obtained through detection of an acoustic wave that is produced by irradiating the specimen with light, the first optical characteristic value distribution being an initial sound pressure distribution or an optical energy absorption density distribution which represents the product of an absorption coefficient distribution and a local fluence distribution;
determining, based on a designation by an operator within the first optical characteristic value distribution, two or more regions of a vessel in the specimen;
determining, from the first optical characteristic value distribution, the initial sound pressure distribution or the optical energy absorption density distribution of the determined two or more regions of the vessel;
calculating, by using the initial sound pressure distribution or the optical energy absorption density distribution of the determined two or more regions of the vessel, an average optical constant of a background region which surrounds the two or more regions of the vessel;
calculating, by using the calculated average optical constant of the background region, the local fluence distribution in the specimen; and
calculating, by dividing the first optical characteristic value distribution by the local fluence distribution, a second optical characteristic value distribution in which the first optical characteristic value distribution is corrected.

15. A non-transitory computer-readable storage medium storing thereon a program that causes a computer to execute the steps of:
calculating a first optical characteristic value distribution in a specimen on the basis of a signal obtained through detection of an acoustic wave that is produced by irradiating the specimen with light, the first optical characteristic value distribution being an initial sound pressure distribution or an optical energy absorption density distribution which represents the product of an absorption coefficient distribution and a local fluence distribution;
determining, based on a designation by on operator within the first optical characteristic value distribution, two or more regions of a vessel in the specimen;
determining, from the first optical characteristic value distribution, the initial sound pressure distribution or the optical energy absorption density distribution of the determined two or more regions of the vessel;
calculating, by using the initial sound pressure distribution or the optical energy absorption density distribution of the determined two or more regions of the vessel, an average optical constant of a background region which surrounds the two or more regions of the vessel;
calculating, by using the calculated average optical constant of the background region, the local fluence distribution in the specimen; and
calculating, by dividing the first optical characteristic value distribution by the local fluence distribution, a second optical characteristic value distribution in which the first optical characteristic value distribution is corrected.

16. An apparatus for obtaining an optical characteristic value distribution in a specimen on the basis of a signal obtained by detection of an acoustic wave generated by irradiation of the specimen with light, comprising:
a memory in communication with a processor, the memory storing instructions that, when executed by the processor, causes the processor to:
calculate, by using the signal, a first optical characteristic value distribution in the specimen, the first optical characteristic value distribution being an initial sound pressure distribution or an optical energy absorption density distribution which represents the product of an absorption coefficient distribution and a local fluence distribution;
determine, based on a designation by an operator within the first optical characteristic value distribution, two or more regions of a vessel in the specimen;
determine from the first optical characteristic value distribution, the initial sound pressure distribution or the optical energy absorption density distribution of the determined two or more regions of the vessel;
calculate, by using the initial sound pressure distribution or the optical energy absorption density distribution of the determined two or more regions of the vessel, an average optical constant of a background region which surrounds the two or more regions of the vessel;
calculate, by using the calculated average optical constant of the background region, the local fluence distribution in the specimen; and
calculate, by dividing the first optical characteristic value distribution by the local fluence distribution, a second optical characteristic value distribution.

17. The apparatus according to claim 16, wherein the first optical characteristic value distribution is an initial sound pressure distribution or an optical energy absorption density distribution which represents the product of an absorption coefficient distribution and a local fluence distribution.

18. The apparatus according to claim 16, wherein the first optical characteristic value distribution is an initial sound pressure distribution or an optical energy absorption density distribution which represents the product of an absorption coefficient distribution and a local fluence distribution.

19. The apparatus according to claim 16, wherein the processor is configured to calculate, on the basis of the first optical characteristic value distribution and the average optical constant of the background region, a second optical characteristic value distribution.

20. The apparatus according to claim 16, wherein the processor is configured to calculate, as the average optical constant, any of an average absorption coefficient, an average scattering coefficient, an average anisotropic parameter, an average reduced scattering coefficient, and an effective attenuation coefficient.

21. An apparatus for obtaining an optical characteristic value distribution in a specimen on the basis of a signal obtained by detection of an acoustic wave generated by irradiation of the specimen with light, comprising:
- a memory in communication with a processor, the memory storing instructions that, when executed by the processor, cause the processor to:
- calculate, by using the signal, a first optical characteristic value distribution in the specimen, the first optical characteristic value distribution being an initial sound pressure distribution or an optical energy absorption density distribution which represents the product of an absorption coefficient distribution and a local fluence distribution;
- determine, on the basis of the first optical characteristic value distribution, two or more regions of a vessel in the specimen;
- determine, from the first optical characteristic value distribution, the initial sound pressure distribution or the optical energy absorption density distribution of the determined two or more regions of the vessel;
- calculate, by using the initial sound pressure distribution or the optical energy absorption density distribution of the determined two or more regions of the vessel, an average optical constant of a background region which surrounds the two or more regions of the vessel;
- calculate, by using the calculated average optical constant of the background region, the local fluence distribution in the specimen; and
- calculate, by dividing the first optical characteristic value distribution by the local fluence distribution, a second optical characteristic value distribution.

22. The apparatus according to claim 21, wherein the first optical characteristic value distribution is an initial sound pressure distribution or an optical energy absorption density distribution which represents the product of an absorption coefficient distribution and a local fluence distribution.

23. The apparatus according to claim 21, wherein the first optical characteristic value distribution is an initial sound pressure distribution or an optical energy absorption density distribution which represents the product of an absorption coefficient distribution and a local fluence distribution.

24. The apparatus according to claim 21, wherein the processor is configured to calculate, on the basis of the first optical characteristic value distribution and the average optical constant of the background region, a second optical characteristic value distribution.

25. The apparatus according to claim 21, wherein the processor is configured to calculate, as the average optical constant, any of an average absorption coefficient, an average scattering coefficient, an average anisotropic parameter, an average reduced scattering coefficient, and an effective attenuation coefficient.

26. An apparatus for obtaining an optical characteristic value distribution in a specimen on the basis of a signal obtained by detection of an acoustic wave generated by irradiation of the specimen with light, comprising:
- a memory in communication with a processor, the memory storing instructions that, when executed by the processor, cause the processor to:
- calculate, using the signal, a first optical characteristic value distribution in the specimen, the first optical characteristic value distribution being an initial sound pressure distribution or an optical energy absorption density distribution which represents the product of an absorption coefficient distribution and a local fluence distribution;
- determine, based on a designation by an operator, two or more regions of a vessel in the specimen;
- determine from the first optical characteristic value distribution, the initial sound pressure distribution or the optical energy absorption density distribution of the determined two or more regions of the vessel;
- calculate, by using the initial sound pressure distribution or the optical energy absorption density distribution of the determined two or more regions of the vessel, an average optical constant of a background region which surrounds the two or more regions of the vessel;
- calculate, by using the calculated average optical constant of the background region, a local fluence distribution in the specimen; and
- calculate, by dividing the first optical characteristic value distribution by the local fluence distribution, a second optical characteristic value distribution.

27. The apparatus according to claim 26, wherein the first optical characteristic value distribution is an initial sound pressure distribution or an optical energy absorption density distribution which represents the product of an absorption coefficient distribution and a local fluence distribution.

28. The apparatus according to claim 26, wherein the first optical characteristic value distribution is an initial sound pressure distribution or an optical energy absorption density distribution which represents the product of an absorption coefficient distribution and a local fluence distribution.

29. The apparatus according to claim 26, wherein the processor is configured to calculate, on the basis of the first optical characteristic value distribution and the average optical constant of the background region, a second optical characteristic value distribution.

30. The apparatus according to claim 26, wherein the processor is configured to calculate, as the average optical constant, any of an average absorption coefficient, an average scattering coefficient, an average anisotropic parameter, an average reduced scattering coefficient, and an effective attenuation coefficient.

* * * * *